United States Patent [19]
Hellberg

[11] Patent Number: 5,846,988
[45] Date of Patent: Dec. 8, 1998

[54] THIAZOLIDINE-4-CARBOXYLIC ACID DERIVATIVES AS CYTOPROTECTIVE AGENTS

[75] Inventor: Mark R. Hellberg, Arlington, Tex.

[73] Assignee: Alcon Laboratories, Inc., Fort Worth, Tex.

[21] Appl. No.: 945,132

[22] PCT Filed: Mar. 19, 1997

[86] PCT No.: PCT/US97/04387

§ 371 Date: Oct. 20, 1997

§ 102(e) Date: Oct. 20, 1997

[87] PCT Pub. No.: WO97/35852

PCT Pub. Date: Oct. 2, 1997

Related U.S. Application Data

[60] Provisional application No. 60/014,027 Mar. 25, 1996.
[51] Int. Cl.$^6$ ................. A61K 31/425; C07D 277/04
[52] U.S. Cl. .............. 514/365; 548/188; 548/194; 548/200; 548/201; 549/408; 514/456
[58] Field of Search .................... 548/188, 194, 548/200, 201; 514/365

[56] References Cited

U.S. PATENT DOCUMENTS

| | | | |
|---|---|---|---|
| 4,550,022 | 10/1985 | Garabedian et al. | 424/127 |
| 4,868,114 | 9/1989 | Nagasawa et al. | 435/112 |
| 4,952,596 | 8/1990 | Della Bella et al. | 514/365 |
| 5,399,573 | 3/1995 | Garner et al. | 514/369 |
| 5,424,321 | 6/1995 | Hellberg et al. | 514/337 |
| 5,589,464 | 12/1996 | Garner et al. | 514/23 |

FOREIGN PATENT DOCUMENTS

| | | |
|---|---|---|
| 0 373 002 A2 | 6/1990 | European Pat. Off. . |
| WO 95/15958 | 6/1995 | WIPO . |

OTHER PUBLICATIONS

Bhuyan et al., "Antioxidant and Anticataractogenic Effects of Topical Captopril in Diquat–Induced Cataract in Rabbits," *Free Radical Biology & Medicine,* vol. 12, pp. 251–261 (1992).

Davison et al., "Active oxygen in neuromuscler disorders," *Molecular and Cellular Biochemistry,* vol. 84, pp. 199–216 (1988).

Nagasawa et al., "Prodrugs of L–Cysteine as Liver–Protective Agents," Journal of Medicinal Chemistry, vol. 25(5), pp. 489–491 (1982).

Nagasawa et al., "2–Substituted Thiazolidine–4–(r)–carboxylic Acids as Prodrugs of L–Cysteine Protection of Mice Against Acetaminophen Hepatotoxicity," *J. Med. Chem.,* vol. 27, pp. 591–596 (1984).

Roberts et al., "L–Cysteine Prodrug Protects Against Cyclophosphamide Urotoxicity Without Compromising Therapeutic Activity," *Cancer Chemother Pharmacol.,* vol. 28; pp. 166–170 (1991).

Roberts et al., "Prodrug of L–Cysteine as Protective Agents Against Acetaminophen–Induced Hepatotoxicity, 2–(Polyhydroxyalkyl)–and–2–(Polyacetoxyalkyl)thiazolidine–4(R)–carboxylic Acids," *J. Med. Chem.,* vol. 30, pp. 1891–1896 (1987).

Santrucek et al., "Antioxidants—Potential Chemotherapeutic Agents, " *Drugs of the Future,* vol. 13(10), pp. 973–996 (1988).

Weber et al., "Thiazolidine–4–carboxylic acid, a physiologic sulfhydrul antioxidant with potential value in geriatric medicine," *Arch. Gerontol. Geriatr.,* vol. 1, pp. 229–310 (1982).

*Primary Examiner*—Johann Richter
*Assistant Examiner*—Laura R. C. Lutz
*Attorney, Agent, or Firm*—Patrick M. Ryan

[57] ABSTRACT

Compounds useful as cytoprotective agents are disclosed. The compounds possess dual activity, containing a phenolic portion selected to have antioxidant or free radical scavenging properties and a thiazolidine-4-carboxylate portion selected for its potential to act as a cysteine prodrug.

13 Claims, No Drawings

THIAZOLIDINE-4-CARBOXYLIC ACID DERIVATIVES AS CYTOPROTECTIVE AGENTS

This application is a 371 of PCT/US97/04387 filed Mar. 19, 1997 which claims priority from U.S. Provisional Application Serial No. 60/014,027 filed Mar. 25, 1996.

FIELD OF THE INVENTION

The present invention relates to pharmaceutical compounds useful in preventing tissue damage induced by oxidative stress. In particular, this invention relates to thiazolidine-4-carboxylic acid derivatives, possessing dual activity as antioxidants and cysteine prodrugs, which are useful as cytoprotective agents.

BACKGROUND OF THE INVENTION

Oxidative stress is known to contribute or lead to a variety of diseases. For a review of diseases and disease conditions associated with oxidative stress, see *Drugs of the Future*, vol. 13 (10), p. 973 (1988) and *Molecular and Cellular Biochemistry*, vol. 84, p. 199 (1988)

Glutathione plays an important role in protecting cellular systems from oxidative damage. Cysteine is an important amino acid and is the rate limiting substrate in the synthesis of glutathione. Cysteine when administered directly can be cytoxic. Prodrug forms of cysteine provide a cysteine delivery system which allows cysteine to be delivered at a rate that reduces cytoxicity and allows for the synthesis of glutathione. Cysteine prodrugs have been demonstrated to be effective in protecting cellular systems from various forms of stress. For these agents to be effective it is necessary for the prodrug to be cleaved either by enzymatic or non-enzymatic means. Once cysteine is released it must be converted into glutathione to demonstrate a therapeutic effect. References to the utility of thiazolidine-4-carboxylates as cysteine prodrugs include *Cancer, Chemotherapy and Pharmacology*, Vol. 28, p. 166 (1991) and *Arch. Gerontology and Geriatrics*, vol. 1, p. 299 (1982).

EP 0 373 002 A2 discloses the use of certain 2-substituted-thiazolidine-4-carboxylic acids as cysteine prodrugs in medicaments for delaying the onset of cataracts in mammals. None of the substituents defined by the reference imparts antioxidant or free radical scavenging properties to the reference 2-substituted-thiazolidine-4-carboxylic acid compounds.

U.S. Pat. No. 4,868,114 discloses a method of stimulating the biosynthesis of glutathione in mammalian cells by contacting the cells with an effective amount of certain L-cysteine prodrugs.

U.S. Pat. No. 4,952,596 discloses N-acyl derivatives of thiazolidine-4-carboxylic acid compounds which possess antipyretic, anti-inflammatory, mucolitic and analgesic activity in addition to activity in the treatment of ischemic pathologies and in pathologies caused by the overproduction of oxidant radicals.

Compounds which are not only capable of supplementing natural defenses against oxidative stress but also capable of protecting cellular systems against acute damage by active oxygen species are desirable.

SUMMARY OF THE INVENTION

The present invention provides compounds which are useful as cytoprotective agents. These compounds possess dual activity as antioxidants and cysteine prodrugs. The antioxidant properties of the compounds of the present invention protect the cellular system against acute damage by active oxygen species or free radicals, while the cysteine prodrug properties supplement the natural defense system by facilitating the synthesis of glutathione.

The present invention also relates to a method of providing cytoprotection to a patient in need thereof. The method comprises administering to such patient a cytoprotective amount of the dual activity compounds of the present invention.

DETAILED DESCRIPTION OF THE INVENTION

The novel compounds of the present invention combine two distinct biologically active moieties in a single chemical entity, and can be represented by the following structural formula

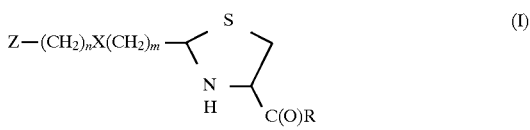

wherein

Z = 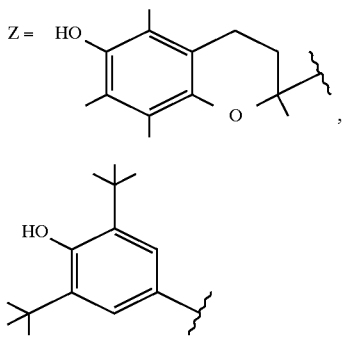

n=0–12;
m=0–12;
X =nothing, $NR^1$, O, or $S(O)_{n'}$; provided that when X=$NR^1$, O, or $S(O)_{n'}$, then m>0 and n>0;
n'=0–2;
$R^1$=H, $C_1$–$C_6$ alkyl;
R=OH or a pharmaceutically acceptable salt thereof, $C_1$–$C_6$ alkoxyl, amino, mono- or dialkylamino where the alkyl has from 1 to 4 carbon atoms, or a radical of an amino acid of the formula:

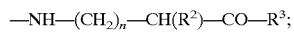

$R^2$=H, $C_1$–$C_4$ alkyl, optionally substituted by hydoxy, SH, $SCH_3$, or (un)substituted phenyl; and
$R^3$=OH, $C_1$–$C_6$ alkoxyl, amino, or mono- or dialkyl amino where the alkyl has from 1 to 4 carbon atoms.

The phenolic portion of the compounds of the present invention is specifically selected to have antioxidant or free radical scavenging activity. The thiazolidine-4-carboxylate is selected for its potential to act as a cysteine prodrug.

Preferred compounds of the present invention are those of formula (I) where n=0–2, m=0–2, X=nothing, R=OH or $C_2$–$C_6$ alkoxy. The most preferred compounds are n=0, m=0, X=nothing, R=OH Compounds of formula (I) may be prepared according to known methods (H. T. Nagasawa, J. C. Roberts, U.S. Pat.

No. 4,868,114) as illustrated below in Scheme 1. Aldehyde (II) is combined with cysteine (commercially available from Aldrich Chemical Company, Milwaukee, Wis., USA ("Aldrich")) in a solvent such as methanol or ethanol and the mixture is warmed at reflux for 0.5–12 h. The reaction mixture is cooled and the carboxylic acid (II, formula (I) where R=OH) is isolated by standard methods. The carboxylic acid (II) can be converted to the ester (formula (I) R=alkoxyl) or amide (formula (I) R=alkyl or dialkyl amine) derivatives by treating the acid (II) with the appropriate alcohol or amine in a solvent such as dimethlyformamide or tetrahydrofuran in the presence of a coupling agent such as dicyclohexylcarbodiimide or 1-(3-dimethylaminopropyl)-3-ethylcarbodimide and 1-hydroxybenzotiazole or 4-dimethylaminopyridine.

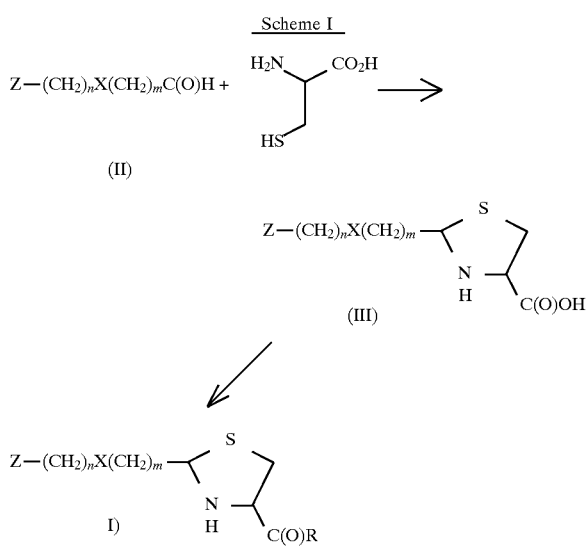

Aldehyde (II) may be prepared as described in Scheme 2. Ester (IV) (M. R. Hellberg, G. Barnes, R. J. Collier, Jr., U.S. Pat. No. 5,424,321) may be reduced to the aldehyde (II) using DIBAL (Aldrich) in a solvent such as methylene chloride at temperatures between −20° and −78° C. Alternately the ester (IV) may be reduced to the alcohol (V) using a reducing agent such as lithium aluminum hydride in a solvent such as tetrahydrofuran and then oxidized to the aldehyde (II) using the Swern oxidation conditions or Collins reagent.

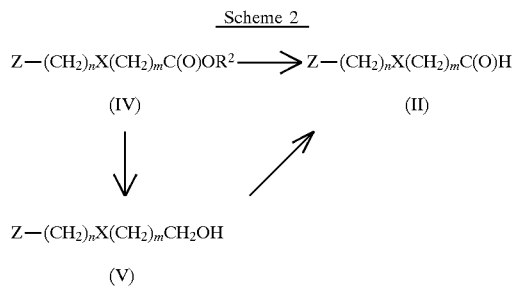

The compounds of formula (I) may be contained in various types of pharmaceutical compositions, in accordance with formulation techniques known to those skilled in the art. For example, the compounds may be included in tablets, capsules, solutions, suspensions and other dosage forms adapted for oral administration, solutions and suspensions adapted for parenteral use; and suppositories for rectal use. Solutions, suspensions and other dosage forms adapted for topical application to the involved tissues, such as tissue irrigating solutions, are particularly preferred for treatment of acute conditions associated with surgery or other forms of trauma.

The present invention is particularly directed to the provision of compositions adapted for treatment of ophthalmic tissues. The ophthalmic compositions of the present invention will include one or more compounds of formula (I) and a pharmaceutically acceptable vehicle for said compound(s). Various types of vehicles may be utilized. The vehicles will generally be aqueous in nature. Aqueous solutions are generally preferred, based on ease of formulation, as well as patients' ability to easily administer such compositions by means of instilling one to two drops of the solutions in the affected eyes. However, the compounds of formula (I) may also be readily incorporated into other types of compositions, such as suspensions, viscous or semi-viscous gels or other types of solid or semi-solid compositions. Suspensions may be preferred for compounds of formula (I) which are relatively insoluble in water. The ophthalmic compositions of the present invention may also include various other ingredients, such as buffers, preservatives, co-solvents and viscosity building agents.

An appropriate buffer system (e.g., sodium phosphate, sodium acetate or sodium borate) may be added to prevent pH drift under storage conditions.

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001% to 1.0% by weight.

Some of the compounds of formula (I) may have limited solubility in water and therefore may require a surfactant or other appropriate co-solvent in the composition. Such co-solvents include: Polysorbate 20, 60 and 80; Pluronic F-68, F-84 and P-103; cyclodextrin; or other agents known to those skilled in the art. Such co-solvents are typically employed at a level of from 0.01% to 10% by weight.

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art. Such agents are typically employed at a level of from 0.01% to 2% by weight.

The pharmaceutical compositions containing one or more compounds of formula (I) may be used to treat patients afflicted with or prone to various types of cellular damage. A representative, but not exhaustive, list of conditions which may be treated with the compounds of the present invention includes: cataract, retinopathies, macular degeneration, damage due to ischemia reprefusion, heart disease, cerebral ischemia, rheumatoid arthritis, cancer, neuromuscular disorders, and atherosclerosis. The concentrations of the compounds in the compositions of the present invention will depend on various factors, including the nature of the condition to be treated with the compositions. However, the compositions will generally contain one or more of the compounds in a concentration of from about 0.001 to about 5 percent by weight, based on the total weight of the composition ("wt. %").

The route of administration (e.g., topical, parenteral or oral) and the dosage regimen will be determined by skilled clinicians, based on factors such as the exact nature of the condition being treated, the severity of the condition, the age and general physical condition of the patient, and so on.

As indicated above, use of the compounds of formula (I) to prevent or reduce damage to ophthalmic tissues at the cellular level is a particularly important aspect of the present invention. Ophthalmic conditions which may be treated include, but are not limited to, cataracts, retinopathies, heredodegenerative diseases, macular degeneration, ocular ischemia, neovascular diseases, glaucoma, and damage associated with injuries to ophthalmic tissues, such as ischemia reperfusion injuries, photochemical injuries, and injuries associated with ocular surgery, particularly injuries to the retina, cornea or other tissues caused by exposure to light or surgical instruments. The compounds may also be used as an adjunct to ophthalmic surgery, such as by vitreal or subconjunctival injection following ophthalmic surgery. The compounds may be used for acute treatment of temporary conditions, or may be administered chronically, especially in the case of degenerative disease. The compounds may also be used prophylactically, especially prior to ocular surgery or noninvasive ophthalmic procedures, or other types of surgery.

The use of physiologically balanced irrigating solutions as pharmaceutical vehicles for the compounds of formula (I) is preferred when the compounds are administered intraocularly. As utilized herein, the term "physiologically balanced irrigating solution" means a solution which is adapted to maintain the physical structure and function of tissues during invasive or noninvasive medical procedures. This type of solution will typically contain electrolytes, such as sodium, potassium, calcium, magnesium and/or chloride; an energy source, such as dextrose; and a buffer to maintain the pH of the solution at or near physiological levels. Various solutions of this type are known (e.g., Lactated Ringers Solution). BSS® Sterile Irrigating Solution and BSS Plus® Sterile Intraocular Irrigating Solution (Alcon Laboratories, Inc., Fort Worth, Tex., USA) are examples of physiologically balanced intraocular irrigating solutions. The latter type of solution is described in U.S. Pat. No. 4,550,022 (Garabedian, et al.).

The doses utilized for any of the above-described purposes will generally be from about 0.01 to about 100 milligrams per kilogram of body weight, administered one to four times per day.

The present invention is further illustrated by means of the following examples. Examples 1–2 illustrate the synthesis of compounds of formula (I); Examples 3–4 demonstrate the physiological activity of the compounds, and methods for measuring that activity; and Example 5 further illustrates the pharmaceutical compositions of the present invention. The following examples are not intended to limit the scope of the invention in any respect.

EXAMPLE 1

Synthesis of (4R)-2-(3,5-di-tert-butyl-4hydroxyphenyl)-4-thiazolidine carboxylic acid A mixture of cysteine (Aldrich, 2.0 g, 17.1 mmol) and 3,5-di-tert-butyl-4-hydroxybenzaldehyde (Aldrich, 4.0 g, 17.1 mmol) in methanol (100 mL) was warmed at reflux for 2.25 h. The reaction mixture was cooled to ambient temperature and the solid that formed upon cooling was collected by filtration. The solid was washed with methanol and recrystallized from a mixture of ethanol/ethyl acetate. Recrystallization from ethanol gave 1.3 g (22% yield) of (4R)-2-(3,5-di-tert-butyl-4-hydroxyphenyl)-4-thiazolidine carboxylic acid as an off white solid, m.p. 163°–165° C.

Elemental Analysis Calculated for $C_{18}H_{27}NO_3S$. Calculated: C, 64.05; H, 8.06; N, 4.15. Found: C, 64.18; H, 8.08; N, 4.09.

EXAMPLE 2

Synthesis of (4R)-2-(6-hydroxy-2,5,7,8-tetramethyl-3,4-dihydro-2H-benzo[1,2-b]pyran-2-yl)-4-thiazolidine carboxylic acid (i) Synthesis of the intermediate 6-hydroxy-2,5,7,8-tetramethyl-3,4-dihydro-2H-benzo[1,2-b]pyran-2-yl methanal:

A solution prepared by the sequential addition of oxalyl chloride (2.9 g, 23 mmol) and dimethyl sulfoxide (3.7 g, 47 mmol) to methylene chloride which had been cooled to −78° C. was allowed to stir for 12 minutes. A solution of 6-hydroxy-2,5,7,8-tetramethyl-3,4-dihydro-2H-benzo[1,2-b]pyran-2-yl methanol (4.0 g, 18 mmol) in 50 mL methylene chloride was then added dropwise to the reaction mixture. After stirring for 40 min., triethylamine (7.3 g, 72.6 mmol) was added dropwise over 5 min. The reaction mixture was stirred at −78° C. for 15 min and then at ambient temperature for 30 min. The reaction mixture was diluted with methylene chloride (100 mL). The resulting solution was washed (water 100 mL, brine 100 mL, water 100 mL), dried (magnesium sulfate), and concentrated under reduced pressure to give a yellow oil. The oil was chromatographed ($SiO_2$, 200 g, ethyl acetate-hexane, 1:9) to give 6-hydroxy-2,5,7,8-tetramethyl-3,4-dihydro-2H-benzo[1,2-b]pyran-2-yl methanal as a white solid (3.0 g, 70% yield).

$^1$H NMR ($CDCl_3$) delta 9.6 (s, 1H), 4.3 (s, 1H), 2.2 (s,3H), 2.1 (s, 3H), 2.2–2.0 (m, 2H), 1.9–1.7 (m, 2H) 1.4 (s, 3H).

(ii) synthesis of (4R)-2-(6-hydroxy-2,5,7,8-tetramethyl-3,4-dihydro-2H-benzo[1,2-b]pyran-2-yl)-4-thiazolidine carboxylic acid A mixture of cysteine (1.5 g, 12.7 mmol) and the intermediate prepared in Example 2 above, 6-hydroxy-2,5,7,8-tetramethyl-3,4-dihydro-2H-benzo[1,2-b]pyran-2-yl methanal (3.0 g, 13 mmol), in methanol was warmed at reflux for 2.5 h. The reaction mixture was cooled to ambient temperature and then stirred at ambient temperature overnight. The reaction mixture was filtered and the filtrate was recrystallized from ethanol (3 times) to give 1.2 g (28% yield) of (4R)-2-(6-hydroxy-2,5,7,8-tetramethyl-3,4-dihydro-2H-benzo[1,2-b]pyran-2-yl)-4-thiazolidine carboxylic acid as a white solid, m.p. 184°–186° C.

Elemental Analysis calculated for $C_{17}H_{23}NO_4S$. Calculated: C, 60.51; H, 6.87; N, 4.15. Found: C, 60.61; H, 6.90; N, 4.17.

The ability of the compounds of formula (I) to function as cytoprotective agents was evaluated as described below in Examples 3 (inhibition of lipid peroxide formation) and 4 (inhibition of lens changes caused by oxidative damage).

EXAMPLE 3

Evaluation of Cytoprotective Ability

Inhibition of lipid peroxide formation by representative compounds of the present invention as compared with the cysteine prodrug, 2-oxo-4-thiazolidine carboxylic acid, (Sigma Chemical Company, St Louis Mo.) is shown in Table 1 below. The cytoprotective effect of the compound was measured using bovine retinal pieces. Retinal tissues were incubated in hypoxic media for 1 h. After 50 min. of hypoxia the test agents were added to the media to allow 10 min. for the drug to diffuse into the tissue prior to reoxygenation. The vehicle by itself, was added to the non-drug group. Following the incubation period, tissue was reoxygenated for 1 h. Lipid peroxidation was assessed by the formation of thiobarbituric acid reacting substances (TBARS). The tissues were homogenized and added to the trichloroacetic acid-thiobarbituric acid reagent and heated in the presence of BHT. The homogenate was filtered and the absorbance of the supernant was measured spectrophotometrically. A double derivative technique was used to calculate the concentration of TBARS present in each sample. Quantiation was based on a molar extinction coefficient of $1.56 \times 10^5$.

TABLE 1

| Compound | % Inhibition of TBARS Production (0.1 mM) | $IC_{50}$ ($\mu M$) |
|---|---|---|
| Example 1 | 95 | 0.05 |
| Example 2 | 90 | 3.0 |
| 2-oxo-4-thiazolidine carboxylic acid | −38 | increased peroxidation |

EXAMPLE 4

Evaluation of Cytoprotective Ability

Inhibition of lens changes caused by oxidative damage by representative compounds of the present invention as compared with the cysteine prodrug, 2-oxo-4-thiazolidine carboxylic acid, (Sigma Chemical Company, St Louis Mo.) is shown in Table 2 below. The cytoprotective effect was measured using excised pigmented rabbit lenses exposed to diquat using the method of Bhuyan (*Free Radical Biology & Medicine*, volume 12, pages 251–261, 1992). Normal lenses were extracted from the eyes immediately after sacrificing the pigmented rabbits. The lens were incubated in modified Krebs-Ringers bicarbonate medium containing 1 mM diquat dibromide monohydrate (Imperial Chemical Industries Ltd., London) and the test compound (1 mM). A non-test drug containing group was used as control. The lenses were incubated for 3 h at 37° C. in a shaking water bath. At the end of the incubation period each lens was removed and homogenated. Glutathione (GSH) and maliondialdehyde (MDA) levels were established by treating the supernatant with trichloracetic acid to precipitate proteins, and then using aliquots of the TCA supernatant to determine glutathione and MDA levels according to standard procedures. Degree of protection was measured as inhibition of GSH loss and inhibition of malondialdehyde formation.

TABLE 2

| Compound | % Inhibition GSH loss | % Inhibition MDA formation |
|---|---|---|
| Example 1 | 40 | 76 |
| 2-oxo-4-thiazolidine carboxylic acid | 9.4 | 28 |

EXAMPLE 5

Representative Formulation

The following formulation is intended to further illustrate the pharmaceutical compositions of the present invention, particularly compositions intended for topical application to the eye. In this example, the term "Compound" is intended to represent any of the compounds of formula (I).

| Ingredient | Amount (wt. %) | Purpose |
|---|---|---|
| Compound (free base) | 1.0 | Active ingredient |
| Polyvinyl alcohol, USP | 1.4 | Excipient |
| Monobasic sodium phosphate (Monohydrate), USP | 0.05 | Buffering agent |
| Dibasic Sodium Phosphate Anhydrous, USP | 0.15 | Buffering agent |
| Sodium chloride, USP | 0.5 | Tonicity agent |
| Disodium EDTA (Edetate disodium, USP | 0.01 | Preservative |
| Polysorbate 80, NF | 0.05 | Surfactant |
| Benzalkonium Chloride Solution, NF | 0.01 + 5 excess | Preservative |
| Sodium hydroxide, NF | q.s. | pH adjustment |
| Hydrochloric acid, NF | q.s. | pH adjustment |
| Water for injection, USP | q.s. | Vehicle |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A compound of the formula

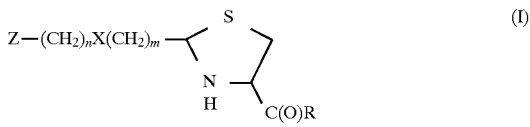

wherein

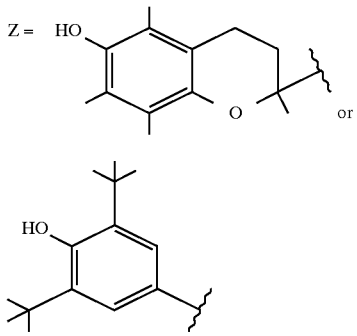

n=0–12;
m=0–12;
X=nothing, $NR^1$, O, or $S(O)_{n'}$; provided that when X=$NR^1$, O, or $S(O)_{n'}$, then m>0 and n>0;
n'=0–2;
$R^1$=H, $C_1$–$C_6$ alkyl;
R=OH or a pharmaceutically acceptable salt thereof, $C_1$–$C_6$ alkoxyl, amino, mono- or dialkylamino where the alkyl has from 1 to 4 carbon atoms, or a radical of an amino acid of the formula:

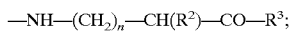

$R^2$=H, $C_1$–$C_4$ alkyl, optionally substituted by hydoxy, SH, $SCH_3$, or optionally substituted phenyl; and $R^3$=OH, $C_1$-$C_6$ alkoxyl, amino, or mono- or dialkyl amino where the alkyl has from 1 to 4 carbon atoms.

2. A compound according to claim 1 wherein n=0–2; m=0–2; X=nothing; and R=OH or $C_2$-$C_6$ alkoxy.

3. A compound according to claim 2 wherein n=0; m=0; X=nothing; and R=OH.

4. A pharmaceutical composition comprising a pharmaceutically acceptable vehicle and a cytoprotective agent of the formula

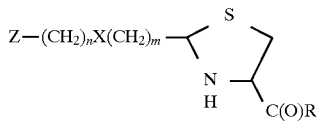  (I)

wherein

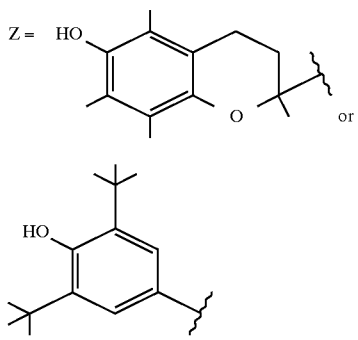

n=0–12;
m=0–12;
X=nothing, $NR^1$, O, or $S(O)_{n'}$; provided that when X=$NR^1$, O, or $S(O)_{n'}$, then m>0 and n>0;
n'=0–2;
$R^1$=H, $C_1$-$C_6$alkyl;
R=OH or a pharmaceutically acceptable salt thereof, $C_1$-$C_6$ alkoxyl, amino, mono- or dialkylamino where the alkyl has from 1 to 4 carbon atoms, or a radical of an amino acid of the formula:

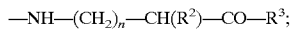

$R^2$=H, $C_1$-$C_4$ alkyl, optionally substituted by hydoxy, SH, $SCH_3$, or optionally substituted phenyl; and
$R^3$=OH, $C_1$-$C_6$ alkoxyl, amino, or mono- or dialkyl amino where the alkyl has from 1 to 4 carbon atoms.

5. A pharmaceutical composition according to claim 4 wherein n=0–2; m=0–2; X=nothing; and R=OH or $C_2$-$C_6$ alkoxy.

6. A pharmaceutical composition according to claim 5 wherein n=0; m=0; X=nothing; and R=OH.

7. A pharmaceutical composition according to claim 4 wherein the composition is adapted for administration to the eye.

8. A pharmaceutical composition according to claim 4 wherein the cytoprotective agent is present in an amount of about 0.001 to about 5% by weight.

9. A method of preventing or treating cataracts, retinopathies, heredodegenerative diseases, macular degeneration, ocular ischemia, neovascular diseases, glaucoma, damage due to ischemia reprefusion, photochemical injuries, heart disease, cerebral ischemia, rheumatoid arthritis, neuromuscular disorders, or atherosclerosis, wherein the method comprises administering to a patient in need thereof a pharmaceutical composition according to claim 4.

10. A method of providing cytoprotection to a patient in need thereof comprising administering to such patient a pharmaceutical composition comprising a pharmaceutically acceptable vehicle and a amount of a cellular protective agent of the formula

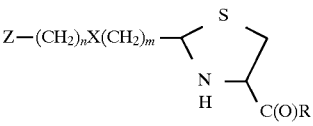  (I)

wherein

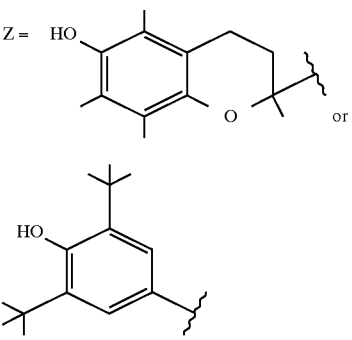

m=0–12;
X=nothing, $NR^1$, O, or $S(O)_{n'}$; provided that when X=$NR^1$, O or $S(O)_{n'}$, then m>0 and n>0;
n'=0–2;
$R^1$=H, $C_1$-$C_6$ alkyl;
R=OH or a pharmaceutically acceptable salt thereof, $C_1$-$C_6$ alkoxyl, amino, mono- or dialkylamino where the alkyl has from 1 to 4 carbon atoms, or a radical of an amino acid of the formula:

$R^2$=H, $C_1$-$C_4$ alkyl, optionally substituted by hydoxy, SH, $SCH_3$, or optionally substituted phenyl; and
$R^3$=OH, $C_1$-$C_6$ alkoxyl, amino, or mono- or dialkyl amino where the alkyl has from 1 to 4 carbon atoms.

11. A method according to claim 10 wherein n=0–2; m=0–2; X=nothing; and R=OH or $C_2$-$C_6$ alkoxy.

12. A method according to claim 11 wherein n=0; m=0; X=nothing; and R=OH.

13. A method according to claim 10 wherein the cytoprotective amount of the cellular protective agent in the pharmaceutical composition is from about 0.001 to about 5% by weight.

* * * * *